United States Patent [19]

King et al.

[11] Patent Number: 4,493,710
[45] Date of Patent: Jan. 15, 1985

[54] INTRAVENOUS DRIP RATE CONTROL DEVICE

[75] Inventors: Roger A. King; John E. Arnold, Jr., both of Minneapolis, Minn.

[73] Assignee: Ivy Medical, Inc., Minneapolis, Minn.

[21] Appl. No.: 550,803

[22] Filed: Nov. 14, 1983

[51] Int. Cl.³ .............................................. A61M 5/00
[52] U.S. Cl. .................................... 604/250; 604/253; 128/DIG. 13; 251/7
[58] Field of Search ................. 128/DIG. 13; 604/60, 604/65–67, 250, 253; 251/4–10

[56] References Cited

U.S. PATENT DOCUMENTS

| | | | |
|---|---|---|---|
| 4,261,388 | 4/1981 | Shelton | 604/253 X |
| 4,312,342 | 1/1982 | Chilkenden | 604/250 X |
| 4,382,453 | 5/1983 | Bujan et al. | 604/250 X |
| 4,425,113 | 1/1984 | Bilstad | 604/250 X |

FOREIGN PATENT DOCUMENTS 2344298 10/1977 France ................................ 604/250

Primary Examiner—Edward M. Coven
Attorney, Agent, or Firm—Herman H. Bains; Malcolm L. Moore; Conrad A. Hansen

[57] ABSTRACT

An intravenous drip rate control device includes a control valve having horizontally oriented valve members each provided with valve elements arranged in interdigitating relation with respect to each other. A drip rate sensor senses each intravenous drip and produces an electrical signal in response to each drip. A microprocessor unit compares the sensed drip rate to a preset drip rate and controls operation of an actuating unit which causes one of the valve members to shift toward and away from the other valve member. When one of the valve members is shifted toward the other valve member, a horizontal portion of the drip tube is progressively stretched to narrow the opening through the stretched portion of the tube and thereby reduce the drip rate. When the valve member is shifted away from the other valve member, the tension on the stretched portion of the tube will be progressively released, thereby increasing the opening in the tube and increasing the drip rate.

7 Claims, 10 Drawing Figures

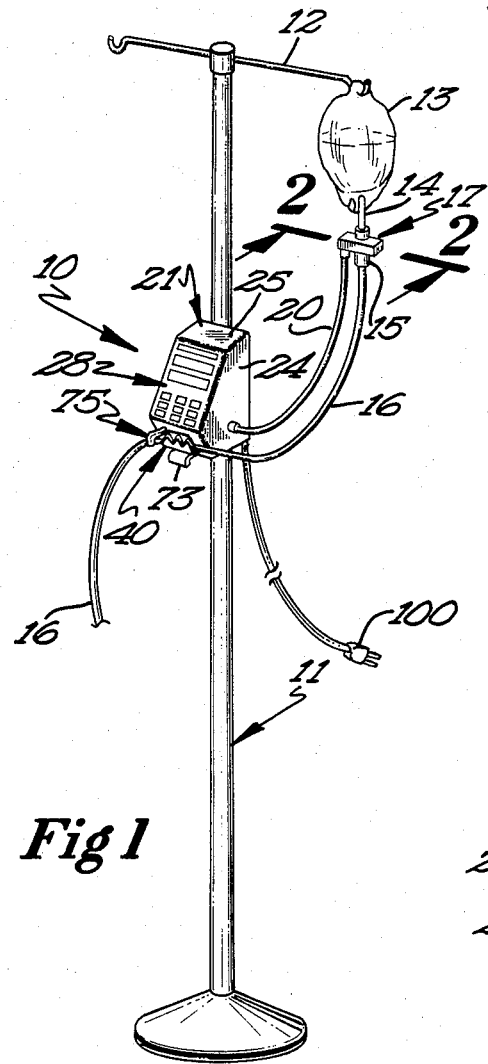
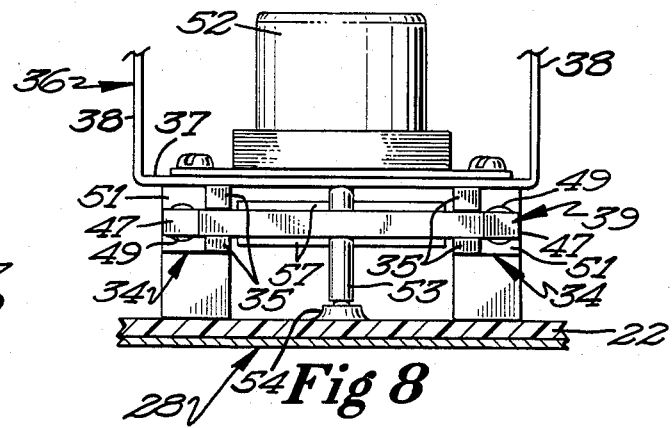
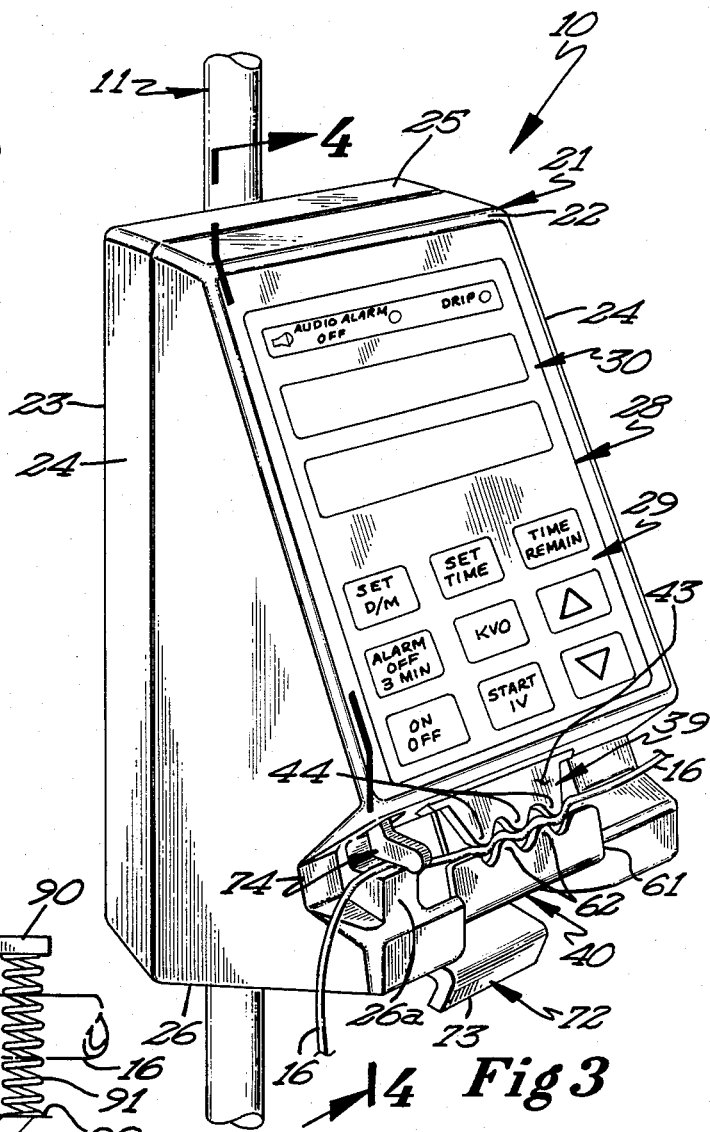
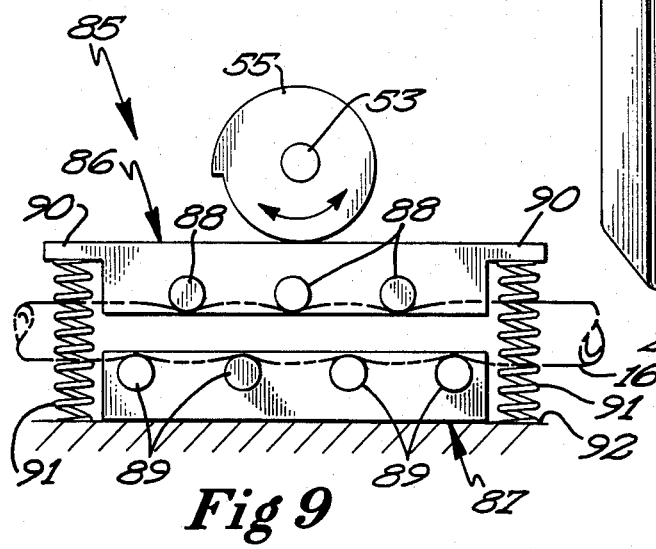

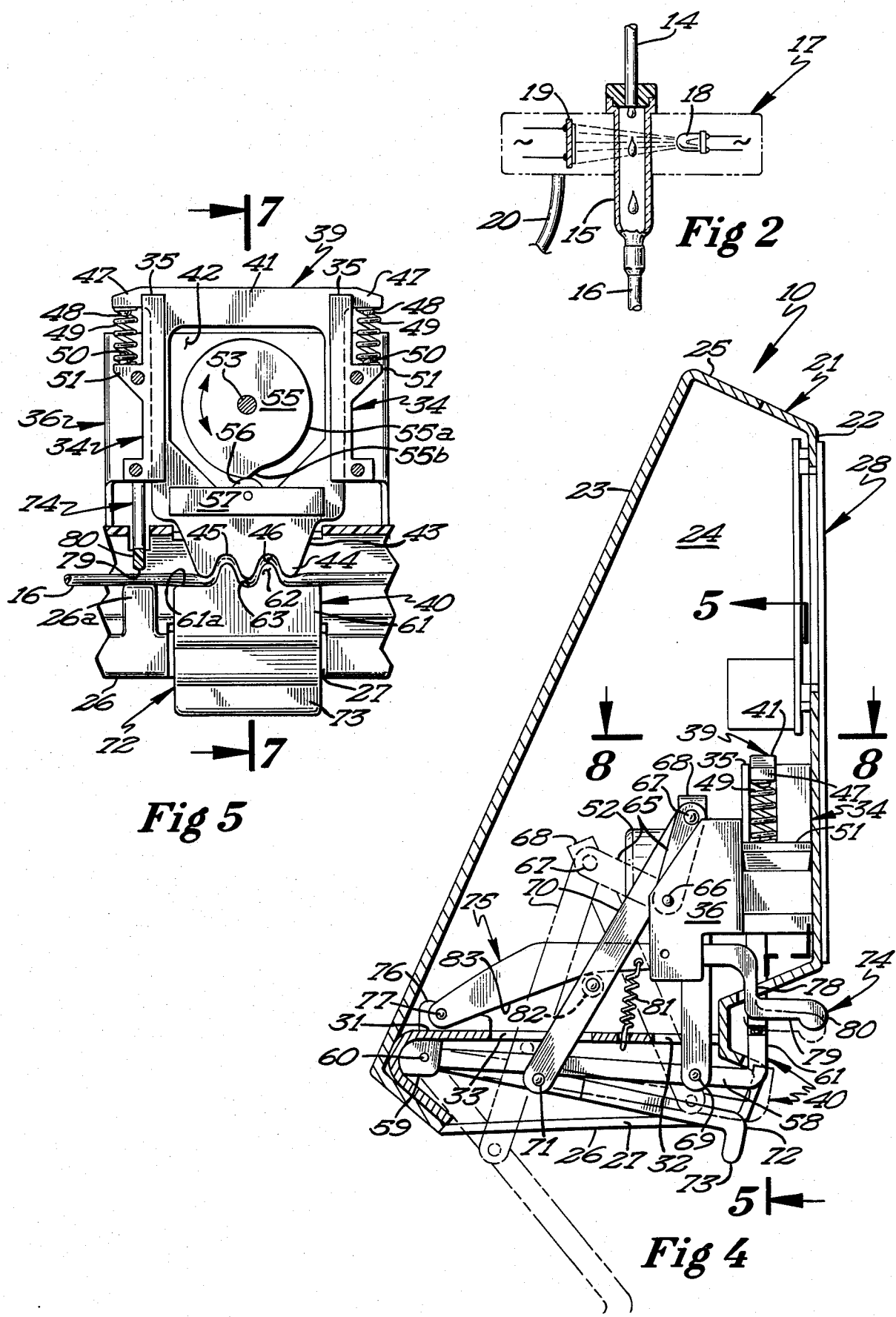

INTRAVENOUS DRIP RATE CONTROL DEVICE

SUMMARY OF THE INVENTION

This invention relates to intravenous feed devices, and more particularly to a controller device for controlling the drip rate of intravenous fluid from a gravity feed container.

Prior art devices have been successfully developed for sensing the drip rate of intravenous fluid from gravity feed containers. One such device is disclosed in U.S. Pat. No. 4,383,252 which accurately senses and monitors the drip rate of the intravenous fluid. However, it is also desirable, and in some instances absolutely essential, to accurately control the drip rate of the I.V. fluid to the patient. Although certain prior art devices have been developed for the purpose of sensing and controlling the drip rate of the intravenous fluid, in many instances this adjustment of the drip rate is done manually by the nursing staff and technicians. Admittedly, this manual adjustment procedure is less than accurate and requires the periodic presence of attendants.

In commercial control devices, the drip tube is mechanically compressed to reduce the rate of flow of the intravenous fluid and the compression applied to the drip tube is decreased to increase the drip rate. A solenoid plunger is typically used in certain of the prior art devices for compressing the drip tube when the drip rate is to be decreased. However, drip tubes are usually formed of plasticized vinyl and these tubes experience cold flow when distorted by compression so that the compressed area of the tube remains in a kinked or pinched condition. Readjustment of such prior art devices requires repositioning of the drip tube by an attendant to permit the solenoid plunger to engage an unkinked portion of the tube. Prior art devices utilizing compression to throttle the drip rate of intravenous fluid are only marginally accurate and do require the periodic presence of an attendant as a result of the distortion of the drip tubes. For example, the state of the art devices are not reliable for prolonged low drip rates of about 3-5 drops per minute. Further, the prior art devices are also incapable of accurate, precise high drip rates of approximately 69 drops per minute.

Other state of the art control devices use a roller clamp which engages the drip tube for controlling the drip rate of the solution. However, the plastic material forming the drip tubes are subject to cold flow, and the drip tubes will eventually close off as a result of cold flow when used with roller clamps.

It is therefore a general object of this invention to provide a control device for gravity feed containers which accurately controls the drip rate of I.V. fluid to a degree which has been heretofore unknown in prior art devices.

A more specific object of this invention is to provide a novel control device which controls the drip rate of the I.V. fluid by gripping and alternately tensioning or untensioning the drip tube to accurately throttle or open the drip tube to conform to a present drip rate.

Another object of this invention is to provide a novel control device which accurately throttles or opens the drip tube to control the drip rate of the I.V. fluid, but which eliminates inadvertent closure resulting from "cold flow" of the material forming the drip tube.

A further object of this invention is to provide a control device which is operable for selectively throttling or opening the drip tube to permit prolonged low drip rates of about 3-5 drops per minute or, alternatively, prolonged high drip rates of up to approximately 200 drops per minute.

Another object of this invention is to provide a control device for a gravity feed container which continuously and automatically senses and adjusts the drip rate of the fluid to a preset rate, and thereby obviates the need of an attendant to check and make such adjustments.

These and other objects and advantages of the invention will appear more fully from the following description made in conjunction with the accompanying drawings wherein like reference characters refer to the same or similar parts throughout the several views.

FIGURES OF THE DRAWING

FIG. 1 is a perspective view of the novel drip rate control device mounted on a stand in flow-controlling relation with respect to the drip tube of a gravity feed container;

FIG. 2 is a fragmentary enlarged diagrammatic view of the photoelectric cell sensing mechanism taken approximately along line 2—2 of FIG. 1;

FIG. 3 is a front perspective view of the control device;

FIG. 4 is a cross-sectional view taken approximately along line 4—4 of FIG. 3 and looking in the direction of the arrows;

FIG. 5 is a cross-sectional view taken approximately along line 5—5 of FIG. 4 and looking in the direction of the arrows;

FIG. 8 is a cross-sectional view taken approximately along line 8—8 of FIG. 4 and looking in the direction of the arrows;

FIG. 9 is a plan view of a modified form of the clamping jaws; and

DESCRIPTION OF THE PREFERRED EMBODIMENT

Figure 6:
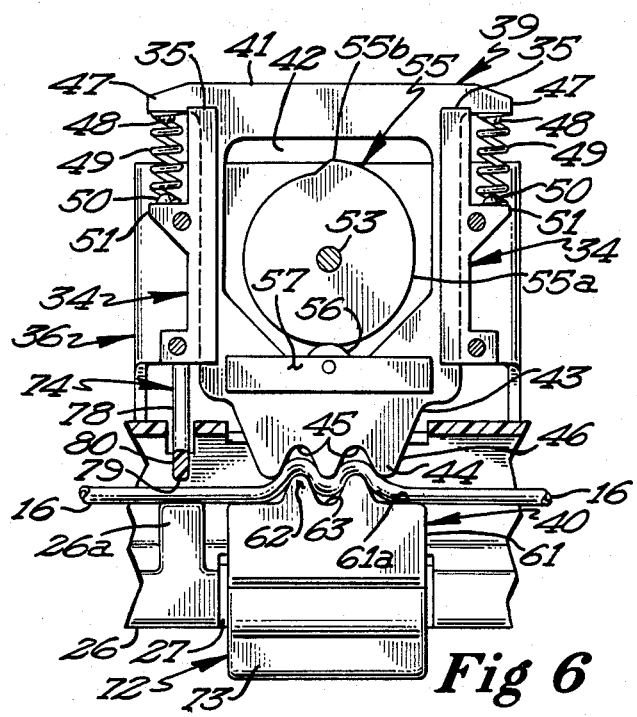
FIG. 6 is a cross-sectional view similar to FIG. 5 but illustrating the clamping jaws of the control device in an open position.
Figure 7:
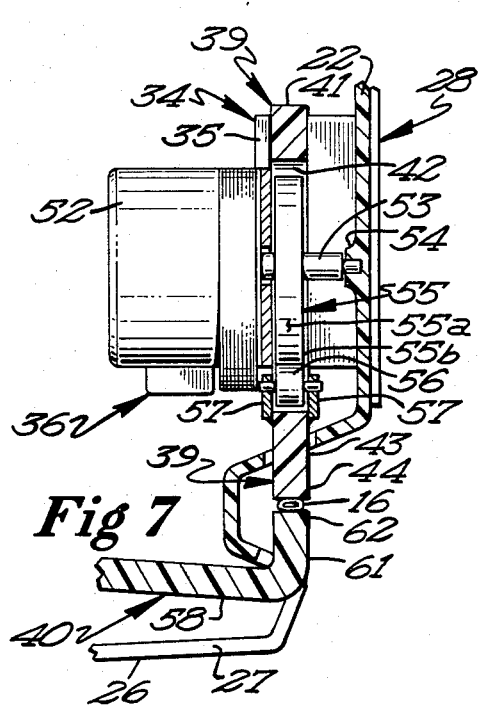
FIG. 7 is a cross-sectional view taken approximately along line 7—7 of FIG. 5 and looking in the direction of the arrows.

Referring now to the drawings, and more particularly to FIG. 1, it will be seen that one embodiment of the novel drip rate controller device, designated generally by the reference numeral 10 is thereshown. The controller device 10 is illustrated as being mounted on an intravenous stand 11, intermediate the ends of the latter. The I.V. stand 11 is provided with a transverse bracket 12 at its upper end which supports an I.V. gravity feed container 13. The I.V. container 13 is adapted to contain a predetermined amount of intravenous fluid, which is discharged therefrom by action of gravity through a feed tube 14 that projects downwardly from the container. The feed tube 14 is connected in communicating relation with a drip chamber 15 to which is connected the upper end of an elongate drip tube 16. The drip tube 16 infuses the fluid into a patient by an intravenous needle in a well-known manner.

A photoelectric cell reader (drop sensor) 17 is mounted on the drip chamber 15 and includes a light emitting diode (LED) 18 and an on-axis and two off-axis photo transistors 19. An electrical conductor cable 20 interconnects the photoelectric cell reader 17 with the controller device 10. The construction and operation of the photoelectric cell reader drop sensor 17 is substantially identical to that disclosed in U.S. Pat. No. 4,383,252, and the disclosure thereof is incorporated herein by reference thereto.

The drip rate controller device 10 includes a housing 21 which is comprised of an inclined disposed front wall 22, a downwardly vertical declined rear wall 23, substantially parallel opposed vertical side walls 24, a top wall 25 and a lower wall 26. It will be seen that the lower wall 26 has a large opening 27 therein. It will also be seen that the bottom wall 26 has an upwardly projecting clamping element 26a integral therewith adjacent the front marginal portion thereof. The purpose of the clamping element 26a will be made more fully known herein below. The front wall 22 of the housing has a control panel or key pad 28 mounted thereon which includes a plurality of touch sensitive switches 29 and which also includes a visual liquid crystal (LCD) display 30. The touch sensitive switches 29 are components of the microprocessor circuitry incorporated in the drip rate controller device 10.

The housing 21 has a horizontally disposed, elongate bracket 31 extending between and secured to the front and rear walls thereof, adjacent but spaced above the bottom wall thereof. The bracket 31 has an opening 32 therethrough adjacent the forward end thereof, and an opening 33 located adjacent the rear end thereof. Referring now to FIGS. 4, 5 and 8, it will be seen that the front wall of the housing 21 has a pair of vertically disposed, laterally spaced apart, substantially parallel guide elements 34 rigidly affixed to the rear surface thereof by suitable securing means such as bolts and the like. Each guide element 34 has a flange 35 integral therewith and projecting inwardly therefrom. A generally U-shaped bracket 36 comprised of a web 37 and opposed, substantially parallel flanges 38 is rigidly secured to the guide elements 34 by bolts, as best seen in FIGS. 4 and 8.

Means are provided for controlling the flow of fluid to the patient, and this means includes a valve comprised of an upper jaw 39 and a lower jaw 40. Referring again to FIG. 4, it will be seen that the upper jaw 39 includes a generally rectangular shaped body 41 having vertical side edge portions thereof that are engaged in the guide elements 34. The upper jaw body 41 is provided with a centrally located opening therein, and also includes a reduced lower portion that defines a jaw element 43. The jaw element 43 is provided with a plurality of alternate projections 44 and recesses 45. Each projection 44 and each recess 45 is smoothly curved so that the projections and recesses present a convoluted surface.

The upper jaw 39 is vertically shiftable along the guide elements 34 and means are provided for yieldably resisting downward shifting movement of the upper jaw. In this regard, it will be noted that the upper end portions of the upper jaw body 41 are provided with outwardly projecting extensions 47, each having a downwardly extending positioning stud 48 depending therefrom. A pair of helical return springs 49 each engage one of the lateral extensions 47 and a positioning stud 48 thereon. The lower end portion of each helical spring also engages a positioning stud 50 on a lateral extension 51 integral with and projecting outwardly of each guide element 34 intermediate the ends thereof. It will therefore be seen that downward shifting movement of the upper jaw is yieldably resisted by the helical springs 49.

Means are provided for shifting the upper jaw in a downward direction against the bias of the helical springs 49, and this means includes a stepping motor 52 which is positioned within the housing 21 and is mounted on the web 37 of the bracket 36. The stepping motor 52 has an output shaft 53 which projects therefrom, and the outer end portion of the output shaft is reduced and projects into a bearing recess 54 formed on the inner surface of the front wall 22.

A rotary cam 55 is keyed to the output shaft 53 of the stepping motor 52 for rotation therewith. The rotary cam has a rotary cam surface 55a which engages a cam follower roller 56 positioned between and journaled on a pair of mounting strips 57. It will be noted that the mounting strips 57 are positioned on opposite sides of the upper jaw body 41 and are secured thereto by any suitable securing means, such as glue or the like. The roller is positioned in the lower reduced portion of the opening 42.

The return springs 49 urge the small cam follower roller 56 into engaging relation with the cam 55. It will be seen that when the stepping motor is energized to rotate the cam 55 in a counter-clockwise direction, as viewed in FIG. 4, the upper jaw will be shifted downwardly. Conversely, when the stepping motor is energized to rotate the cam 55 in a clockwise direction, the follower-type roller 56 will follow the cam surface and will be shifted upwardly by the action of the helical springs 49.

The lower jaw 40 includes a generally rectangularly shaped body 58 which is positioned in the housing 21 and extends in a fore and aft direction. The rear end portion of the lower jaw body 58 is pivotally connected to a pair of brackets 59 by pivots 60 to permit vertical swinging movement of the lower jaw between an operative and inoperative, fully open position. It will be seen that the brackets 59 are secured to the bracket 31, as best seen in FIG. 5. It will be noted that the lower jaw projects exteriorly of the housing 21 and terminates in a vertical jaw element 61 which is disposed in generally opposed relation with respect to the upper jaw 39. The vertical jaw element 61 is of generally rectangular configuration and has a pair of laterally spaced apart projections 62 integral therewith and projecting upwardly therefrom. It will be noted that a recess 63 is defined between the projections 62, and that the recess 63 and projections 62 are characterized by smoothly curved, contoured faces that define a convoluted surface. It will be seen that the projections 44 and recesses 45 on the upper jaw interdigitate with the projections and recesses on the lower jaw element and engage the drip tube which extends between the jaws.

Means are provided for manually shifting the lower jaw vertically about its pivotal axis 60 between the upper operative position and the lower inoperative position. This means includes a pair of over-center linkages each suspending the lower jaw with the U-shaped bracket 36. The linkages on each side of the lower jaw are identical, and each includes a link 65 which has one end pivotally connected by a pivot 66 to one of the flanges 38 of the bracket 36. The other end of each link 65 is connected by a pivot 67 to one end of an elongate link 68, as best seen in FIG. 5. It will be noted that the link 68 is substantially longer than the link 65 and has its other end pivotally connected by pivot 69 to the lower jaw body 58 adjacent the front end of the latter. One end of an elongate link 70 is also pivotally connected to the pivot 67 which interconnects the link 65 and the link 68. The lower end of the link 70 is pivotally connected by pivot 71 to an elongate lower jaw-opening lever 72 intermediate the ends of the latter. It will be seen that the opening lever has one end pivotally connected to the pivot 60 which pivotally mounts the lower jaw to the housing 21. The opening lever projects through the recess 27 and has a down-turned front end portion 73 to facilitate gripping the lever.

The linkage actuating lever and lower jaw are illustrated in the upper operative position by full line configuration in FIG. 5. It will be seen that when the actuating lever 72 is moved downwardly by a user, the lower jaw will be swung to the lower inoperative, fully open position. The over-center linkages 64 will be swung from the full line position to the dotted line position. It will further be noted that when the linkage 64 is in the full line position, as illustrated in FIG. 5, the pivot point 66 is disposed in over-center relation with respect to the pivotal axes 67 and 69.

The drip rate controller device 10 is also provided with a safety valve 74 which includes an elongate lever 75 pivotally connected by a pivot 77 to a bracket 76 mounted on the upper surface of the bracket 31 adjacent the rear end thereof. The valve lever 75 projects forwardly from its pivotal connection and includes a downturned portion adjacent the front end thereof which defines a vertical valve element 78. The vertical valve element 78 is provided with a pinching surface at its lower end and is integral with a gripping element 80 which projects forwardly of the vertical valve element 78 and exteriorly of the housing 21.

A coil spring 81 is interconnected to the lever 75 intermediate the ends thereof and is also connected to the bracket 31 and is operable to urge the lever 75 in a downward direction about its pivotal axis 77. It will be noted that the safety valve 74 is located adjacent one side of the housing 21 and is urged by the spring 81 into engaging relation with a cam roller 82 which is mounted on the adjacent link 70. It will therefore be seen that when the opener lever 72 is moved downwardly to shift the lower jaw to the lowered inoperative position, the lower camming surface 83 of the lever 75 will follow the cam roller 82 downwardly as a result of the action of the spring 81. Thus the safety valve will be moved downwardly so that the pinching surface will engage the clamping element 26a.

It will be appreciated that the drip tube will be passed horizontally between the convoluted surfaces defined by the upper and lower jaws of the control valve, and will also be positioned upon the upper surface of the clamping element 26a. Therefore, when the lower jaw is in the fully open position, the safety valve will pinch off the drip tube to close the same and prevent runaway flow in the event that the opening lever is accidentally moved downwardly to the lower inoperative, fully open position.

Referring now to FIG. 9, it will be seen that a modified form of the drip rate control valve is thereshown, and is designated generally by the reference numeral 85. The valve 85 also includes an upper jaw 86 and a lower jaw 87. The upper jaw 86 is of generally rectangular configuration, and is provided with a plurality of laterally spaced apart pins 88 that are affixed thereto and project in a fore and aft direction therefrom. The lower jaw 87 is also provided with a plurality of laterally spaced apart similar pins 89 which are affixed thereto and project in a fore and aft direction therefrom. In the embodiment shown, the upper jaw is provided with three pins and the lower jaw is provided with four pins. The spacing of the pins on the jaws disposes the pins in interdigitating relation in the manner of the convoluted jaw surfaces on the upper and lower jaws of the embodiments of FIGS. 1 through 8.

The upper jaw 86 is also provided with lateral extensions 90 which project laterally outwardly from the upper corner portion thereof, and which engage the upper ends of a pair of helical springs 91. The lower ends of the helical springs engage the support 92 which supports the control valve 85 and to which the lower jaw 87 is mounted. The upper surface of the upper jaw 86 may be engaged by a rotary cam 55 which is keyed to the output shaft 53 of the stepping motor 52. It will be seen that rotation of the cam 55 in one direction shifts the upper jaw 86 towards the lower jaw against the bias of the helical spring 91. The rotation of the rotary cam in the opposite direction results in shifting of the upper jaw away from the lower jaw by the action of the helical springs 91. Alternatively, the valve 85 may be operated manually to shift the upper jaw 86 towards and away from the lower jaw 87. When the valve 85 or the valve of the embodiment of FIG. 1 is operated manually, the operator will adjust the upper jaw relative to the lower jaw by visually observing the drip rate and shifting the upper jaw accordingly.

It will also be noted that the interdigitating relation of the pins 88 and 89 produce a stretching action with respect to the tube 16 in the same manner as the interdigitating convoluted elements on the upper jaw 39 and lower jaw 40 in the previously described embodiment. This stretching of the drip tube 16 throttles or narrows the lumen of the tube and therefore reduces the drip rate through this stretched portion of the tube. Conversely, a relaxation of the tension on the tube permits the tube to tend to return to its original shape and therefore increase the cross-sectional area of the lumen of the tube through the stretched portion.

Figure 10:
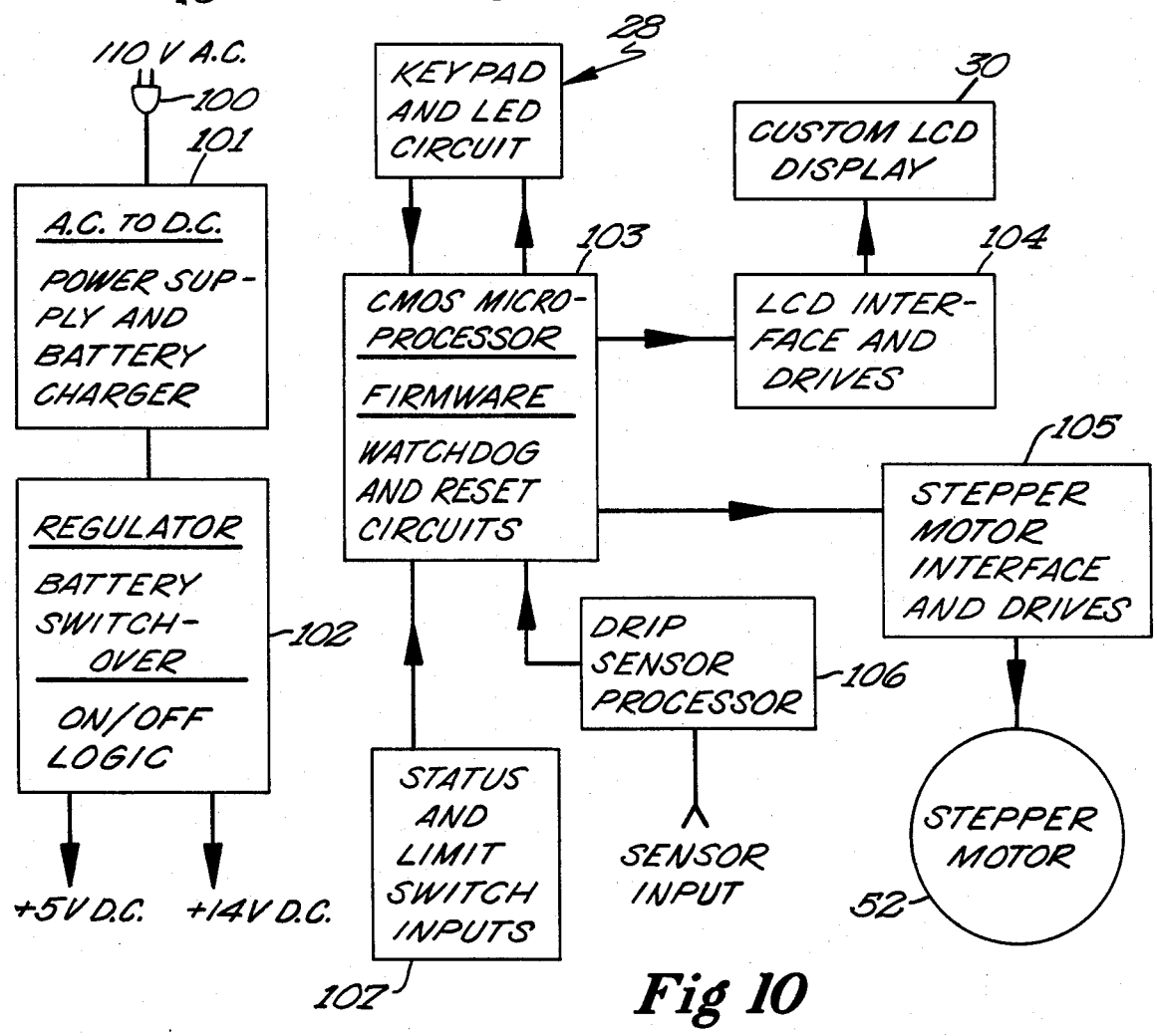
FIG. 10 is a block diagram of the electrical circuitry of the apparatus.

Referring now to FIG. 10, it will be seen that the electrical circuit block diagram for the drip rate controller device is thereshown. The circuitry includes a converter and battery charger unit 101 which is operable to convert AC to DC, and also provides a battery charging function. A suitable electrical conductor 100 having a conventional bayonet type plug is provided for supplying the line power to the unit. The converter and battery charger unit 101 is electrically connected to a regulator/battery switchover/on-off logic unit 102. This unit permits the controller device to be operated on battery or line power. The unit also automatically switches the controller to battery in the event that line power to the unit is interrupted. It will be noted that this unit produces a 5 V DC output and a 14 V DC output for operating the various components of the circuitry. In this regard, the low voltage output provides power to the display and interface and drives therefore. The higher voltage output is used to energize the drip rate sensor and the stepper motor 52.

Output signals from the drip rate sensor 17 are directed to a drip sensor processor 106 and the output therefrom is directed to the CMOS microprocessor/firmware/watch dog and reset circuits 103. The microprocessor unit 103 is electrically connected to the key pad and LED circuit 28. The microprocessor unit 103 is also connected to an LCD interface and drive unit 104 which is electrically connected to the custom liquid crystal (LCD) display 30.

The microprocessor unit is electrically connected to the stepper motor interface and drive unit 105 which controls the stepper motor 52. Status and limit switch inputs 107 are electrically connected to the microprocessor unit. In this regard, the settable range shall be from KVO (3 drops/minute) to 200 drops/minute, and it has been found that the device is effective to control within 1-2% across this range. The symbol KVO designates the rate needed to keep the vein open so as to obviate the need for reinsertion of the needle into the vein. This rate has been found to be 3 drops/minute.

In operation, the operator will actuate the On-Off switch to energize the circuitry for the drip rate controller device. The operator will then actuate the Set D/M (drops per minute), and this initializes the memory to accept a rate value for infusion in drops per minute. The set rate may be changed by decreasing or increasing the rate, as desired. To increase the drip rate, the operator will actuate the increase button illustrated by the triangle having the apex pointed upwardly. The decrease button is designated by a triangle with the apex pointing downwardly. The increase or decrease button will increase or decrease the value being programmed as long as the button remains depressed. The operator will also actuate the Set Time and Time Remain buttons. The respective values will be displayed on the custom LCD display 30. The operator will actuate the Start I.V. to start the intravenous operation. At the beginning, the upper and lower jaws will be in substantially closed condition so that the drip rate is approximately 12 drops per minute. Thereafter, the output signals from the drip rate sensor 17 will be received by the drip sensor processor and thereafter by the microprocessor and compared to the preset drip rate. The stepper motor will then be energized to operate the valve in response to this comparison. If the sensed drip rate is greater than the set drip rate, then the cam 55 will be rotated in a direction to progressively move the upper jaw towards the lower jaw. When this occurs, the interdigitating jaw surfaces of the upper and lower jaw will progresssively engage the tube and will stretch the tube, thereby progressively decreasing the lumen or opening through the stretched portion. This produces a throttling effect with respect to the intravenous fluid which drips through the stretched portion. The stepper motor will rotate the cam the desired degree until the sensed drip rate conforms to the preset drip rate. It is pointed out that when the Off button is pushed, the jaws will be clamped closed and thereby shut off the flow of fluid through the tube.

If the sensed drip rate is less than the preset drip rate, the stepper motor 52 will rotate the cam in a direction so that the helical springs 49 will urge the upper jaw progressively away from the lower jaw. As this occurs, the tension on the drip tube will lessen and the inherent memory characteristics of the elastic drip tube will permit the drip tube to tend to return to its original shape, thereby increasing the opening or lumen through the stretched portion. Thus the drip rate through this stretched portion will increase.

The microprocessor unit 103 is also provided with watch dog and reset circuits whose logic is operable to initiate audible and visual alarms. The visual alarm is displayed on the controller unit. There are two levels of alarm status, including a low priority which is indicated by a one-half second audible tone once each minute while lighting the corresponding arrow message on the control panel. There is also a high priority alarm which will be indicated by a one-half second audible tone every second while simultaneously lighting the corresponding arrow message on the control panel.

There are various alarm conditions, including a no-drop condition, which is a high priority alarm and would be triggered by the lack of a signal change by the drop rate sensor after the Start I.V. button is actuated. A runaway condition occurs and is detected by a rapid rate increase in the drop signal, and this is programmed as a high priority alarm. A high priority alarm signal will be given in the event of an occlusion which is initiated by the detection of slowing of the drop rate to a very low rate with the control valve open during the first 20 minutes of infusion. Low priority alarms occur when there is a set-up error, a rate deviation, or a low battery condition. It is pointed out that if there is a high priority alarm, the microprocessor circuit will actuate the stepper motor to cause the control valve to close to the KVO (keep vein open) rate of 3 drops/minute. However, the circuitry will not operate during the low priority alarm to achieve KVO.

From the foregoing it will be noted that we have provided a novel drip rate controller device which is operable to control the selected drip rate within 1-2% accuracy. The drip rate control device does not require the attention of an attendant during its operation except in an alarm condition. Thus our drip rate device is especially adapted for institutions that do not have large staffs.

It will also be seen that our novel drip rate control device utilizes the unique concept of stretching a portion of the drip tube to automatically control the drip rate through the tube. This is in sharp distinction to the prior art systems that grip or pinch the drip tube and produce semi-permanent distortion of the drip tube.

Thus it will be seen that we have provided a novel drip rate control device which is not only of simple and inexpensive construction and operation, but one which functions in a more efficient manner than any heretofore known comparable device.

While the preferred embodiments of the present invention have been described, it should be understood that various changes, adaptions and modifications may be made therein without departing from the spirit of the invention and the scope of the appended claims.

What is claimed is:

1. An intravenous drip rate controller device for use in controlling the drip rate of a solution from an intravenous container mounted on an intravenous pole stand and having a drip chamber connected in fluid flow relation with said intravenous chamber, a flexible elastic drip tube connected to the drip chamber and extending downwardly therefrom, and a drip rate sensing means positioned in proximity to the drip chamber for sensing each intravenous drip and generating an electrical signal in response to each drip indicative of the drip rate, said device comprising:

a support structure mounted on said intravenous pole stand, a control valve on said support for controlling the drip rate of the solution including opposed valve members each having projections and recesses arranged in interdigitating relation with the projections and recesses on the other valve member to define undulating clamping surfaces, means supporting one of said valve members for shifting movement of said one valve member toward and away from the other valve member whereby when said one valve member is shifted toward the other valve member, a portion of the drip tube extending horizontally between and along said undulating clamping surfaces of the valve members will be engaged and stretched in a direction longitudinally of the tube by the interdigitating projections and recesses defining the undulating clamping surfaces to progressively reduce the opening in that length of the drip tube engaged by the undulating clamping surfaces to thereby reduce the drip rate through the stretched portion, and when one said valve member is shifted away from the other valve member, the tension on the elastic drip tube will be progressively relaxed to permit the drip tube to return to its original unstretched condition and thereby increase the drip rate of the solution passing therethrough.

2. An intravenous drip rate controller device for use in controlling the drip rate of a solution from an intravenous container mounted on an intravenous pole stand, a drip chamber connected in communicating relation with said intravenous chamber, a flexible elastic drip tube connected to the drip chamber and extending downwardly therefrom, and a drip rate sensing means positioned in proximity to the drip chamber for sensing each intravenous drip and generating an electrical signal in response to each drip, said device comprising:
 a support structure mounted on the intravenous pole stand,
 a control valve on said support for controlling the drip rate of the solution including opposed valve members each having projections and recesses arranged in interdigitating relation with the projections and recesses on the other valve member to define undulating clamping surfaces,
 actuating means operatively engaging said one valve element for shifting the same toward and away from the other valve element,
 control means electrically connected with said drip sensing means for receiving signals from the latter and comparing the sensing drip rate to a preselected drip rate, said control means being operable if said sensed drip rate is greater than said preselected drip rate to operate the actuating means and shift said one valve member toward the other valve member whereby a portion of the drip tube extending horizontally between and along said undulating clamping surfaces of the valve members will be engaged and stretched in a direction longitudinally of the tube by the interdigitating projections and recesses defining the undulating clamping surfaces to reduce the opening in the drip tube until the sensed drip rate through the stretched horizontal portion of the drip tube conforms to the preselected drip rate, and said control means being operable when the sensed drip rate decreases to operate said actuating means to cause said one valve member to move away from the other valve member to decrease the tension on the horizontal portion of the drip tube and thereby permit the horizontal portion of the drip tube to progressively return to its untensioned condition and increase the opening therethrough and thereby increase the drip rate through the horizontal portion.

3. An intravenous drip rate controller device as defined in claim 2 wherein said valve members arranged in upper and lower relationship, said lower valve member being shiftable between a raised operative position and a lowered inoperative position, said upper valve member being shiftable towards and away from said lower valve member by said actuating means when said lower valve member is in the raised operative position.

4. The intravenous drip rate controller device as defined in claim 3 and a safety valve member shiftably mounted on said support structure for shifting movement between open and closed positions, said safety valve member when in the closed position compressing said drip tube to close the same and being retracted out of non-compressing relation with the drip tube when in the open position.

5. The intravenous drip rate controller device as defined in claim 6 and means operatively interconnecting said safety valve member with said lower valve member and being operable to shift the safety valve member to a closed position when said lower valve member is shifted to a lowered inoperative position.

6. The intravenous drip rate controller device as defined in claim 2 and means for normally urging said upper valve member away from said lower valve member, said actuating means including a reversible electric motor, a rotary cam connected with said motor and being revolved thereby and engaging said upper valve member for shifting the latter toward the lower valve member when said cam is rotated in one direction, and permitting shifting of the upper valve member away from said lower valve member when said cam member is rotated in the opposite direction.

7. A control valve for controlling the drip rate of the solution from an intravenous container having a drip chamber and having a drip tube connected to the drip chamber and extending therefrom, comprising:
 a pair of opposed valve members each having projections and recesses arranged in interdigitating relation with the projections and recesses of the other valve member to define undulating clamping surfaces, one of said valve members being shiftable toward and away from the other valve member whereby when said one valve member is shifted toward the other valve member, a portion of the drip tube extending horizontally between and along said undulating clamping surfaces of the valve members will be engaged and stretched in a direction longitudinally of the tube by the interdigitating projections and recesses defining the undulating clamping surfaces of the valve members to progressively reduce the opening in that length of the drip tube engaged by the valve elements to thereby reduce the drip rate through the stretched portion, and when said one valve member is shifted away from the other valve member, the tension on the elastic drip tube will be progressively relaxed to permit the drip tube to return to its original unstretched condition and thereby increase the drip rate of the solution passing therethrough.

* * * * *